US012118868B2

(12) United States Patent
Mueller et al.

(10) Patent No.: US 12,118,868 B2
(45) Date of Patent: Oct. 15, 2024

(54) CHILD MONITORING DEVICES AND SYSTEMS

(71) Applicant: THE BABYPLUS COMPANY, LLC, Fishers, IN (US)

(72) Inventors: Karl-Heinz Mueller, Fishers, IN (US); Julie Louly, Fishers, IN (US)

(73) Assignee: The BabyPlus Company, LLC, Fishers, IN (US)

( * ) Notice: Subject to any disclaimer, the term of this patent is extended or adjusted under 35 U.S.C. 154(b) by 89 days.

(21) Appl. No.: 18/016,448

(22) PCT Filed: Feb. 9, 2021

(86) PCT No.: PCT/US2021/017281
§ 371 (c)(1),
(2) Date: Jan. 16, 2023

(87) PCT Pub. No.: WO2022/015372
PCT Pub. Date: Jan. 20, 2022

(65) Prior Publication Data
US 2023/0260382 A1    Aug. 17, 2023

Related U.S. Application Data

(60) Provisional application No. 63/052,621, filed on Jul. 16, 2020.

(51) Int. Cl.
*G08B 21/12* (2006.01)
*A61B 5/00* (2006.01)
(Continued)

(52) U.S. Cl.
CPC ............ *G08B 21/12* (2013.01); *A61B 5/4815* (2013.01); *G01N 33/0004* (2013.01);
(Continued)

(58) Field of Classification Search
CPC  G08B 21/12; G08B 21/0208; G08B 21/0211; G08B 21/0277; A61B 5/4815; G01N 33/0004
See application file for complete search history.

(56) References Cited

U.S. PATENT DOCUMENTS

2009/0121826 A1*  5/2009  Song .................... A61B 5/6887
                                                  340/3.1
2010/0030382 A1*  2/2010  Shalat .................... B25J 13/087
                                                  901/1

(Continued)

FOREIGN PATENT DOCUMENTS

WO       2020/055872       3/2020

*Primary Examiner* — An T Nguyen
(74) *Attorney, Agent, or Firm* — Thibault Patent Group

(57) ABSTRACT

A child monitoring device has a plurality of sensors to sense data relating to a child to be monitored, a wireless communications unit and a processing unit. The processing unit is able to receive signals from the sensors, receive data relating to the child input via said wireless communications unit, cause the wireless communications unit to wirelessly communicate with an external database to receive data, process the signals received from said sensors to determine child development conditions, compare determined child development conditions with the data received from external database, and cause said wireless communications unit to transmit messages containing child development information for reception by an external device.

10 Claims, 3 Drawing Sheets

(51) Int. Cl.
*G01N 33/00* (2006.01)
*G08B 21/02* (2006.01)

(52) U.S. Cl.
CPC ...... *G08B 21/0208* (2013.01); *G08B 21/0211* (2013.01); *G08B 21/0277* (2013.01)

(56) References Cited

U.S. PATENT DOCUMENTS

2015/0288877 A1* 10/2015 Glazer .................. H04N 7/183
 348/77
2016/0324466 A1* 11/2016 Chang .................. A61B 5/4806
2017/0104916 A1 4/2017 Mueller

* cited by examiner

CHILD MONITORING DEVICES AND SYSTEMS

FIELD OF THE INVENTION

The invention relates to child monitoring devices and systems.

BACKGROUND TO THE INVENTION

Parents, especially with a first-born child, tend to be anxious as to whether their child's growth and development of skills are normal. There are many factors that influence a child's development. It would be a considerable burden for parents to have to monitor growth and development milestones involved and to then analyse them and determine how their child is progressing when compared to the children of the same age. One of the reasons for well-child visits to the pediatrician in the early years is to monitor a child's development.

SUMMARY OF THE INVENTION

Examples of the invention provide a child monitoring device comprising:
- at least one environmental sensor to output signals representative of an environmental condition in an indoor space in which the child monitoring device is located;
- a wireless communications unit; and
- a processing unit,
- wherein said processing unit is configured to:
- receive said signals from said at least one environmental sensor and process said signals to determine an indoor space air quality condition,
- cause said wireless communications unit to wirelessly communicate with an external database to receive data indicative of an outdoor air quality condition at a location at which said indoor space is located and data correlating air quality to child development,
- process said indoor air quality condition, outdoor air quality condition and data relating air quality of child development to determine whether said indoor air quality condition is within predetermined limits, and
- if said indoor air quality is not within said predetermined limits cause said wireless communications unit to output messages indicating adjustments to cause a change in said indoor space air quality condition to provide an indoor space air quality condition that is within said predetermined limits Examples of the invention provide a child monitoring device, said child monitoring device comprising:
- a plurality of sensors to sense data relating to a child to be monitored;
- a wireless communications unit; and
- a processing unit,
- wherein said processing unit is configured to:
- receive said signals from said sensors,
- receive data relating to said child input via said wireless communications unit;
- cause said wireless communications unit to wirelessly communicate with an external database to receive data,
- process said signals received from said sensors to determine child development conditions,
- compare said determined child development conditions with said data received from said external database, and
- cause said wireless communications unit to transmit messages containing child development information for reception by an external device.

Examples of the invention provide a child monitoring device, said child monitoring device comprising:
- a plurality of sensors to sense data relating to a child to be monitored;
- a communications unit configured to transmit and receive via the internet; and
- a processing unit,
- wherein said processing unit is configured to:
- receive said signals from said sensors,
- receive data relating to said child input via said wireless communications unit;
- cause said wireless communications unit to wirelessly communicate with an external database to receive data,
- process said signals received from said sensors to determine child development conditions,
- compare said determined child development conditions with said data received from said external database, and
- cause said wireless communications unit to transmit messages containing child development information for reception by an external device.

Examples of the invention may be embodied in a computer program product, or app, comprising at least one computer program software portion which, when executed in an execution environment, is operable to control a processing unit as described in any of the last three preceding paragraphs.

Examples of child monitoring devices according to the invention may provide information and guidelines to parents that allow them to judge and improve their child's development. The child monitoring device may use different sensors to collect data, which is processed and analysed. The processed data and environmental data drawn from one or more external databases may be compared with an expert database, which contains data concerning normal child development. The child monitoring device may incorporate AI functions, which verify the consistency of at least a part of the data, so that erroneous readings can be identified. Once data verification shows consistency, the analysis will determine any deviation from normal child development that needs to be addressed and which surrounding factors could have influence.

BRIEF DESCRIPTION OF THE DRAWINGS

In order that the invention may be well understood, some examples thereof, which are given by way of example only, will now be described with reference to the drawings in which.

DETAILED DESCRIPTION

Figure 1:
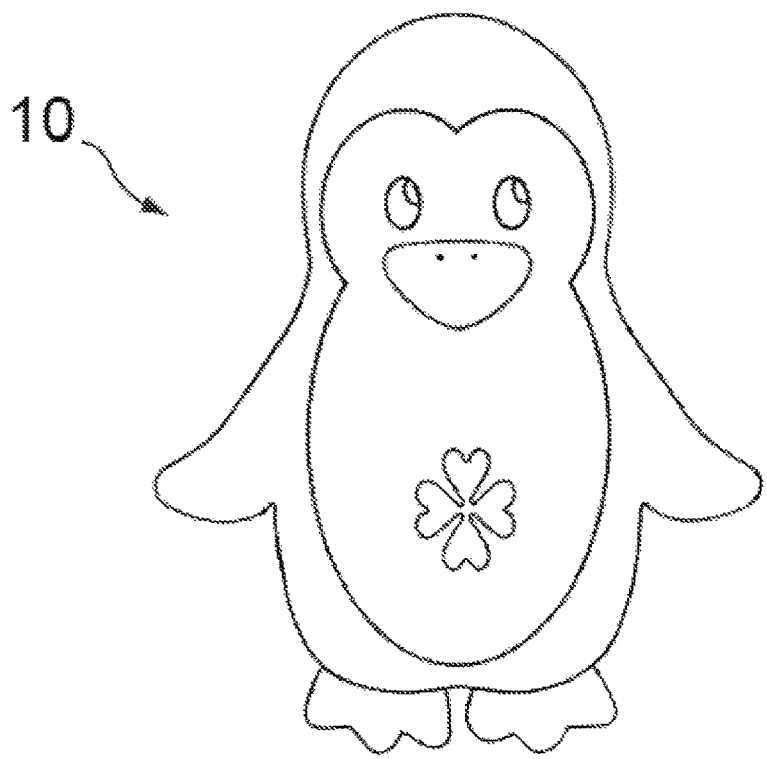
FIG. 1 is a view from the front of a toy incorporating a child monitoring device.

Referring to FIG. 1, a toy 10 may incorporate a child monitoring device as described below with reference to FIGS. 3 and 4. The toy 10 may take the form of an animal such as a bird, for example, a penguin. The toy 10 may be made of a plastics material. It is to be understood that in the context of the present invention, examples may be used to monitor an unborn child (foetus) and in context references to a child in the present application, including the claims are to be understood as extending to cover a foetus.

Figure 3:
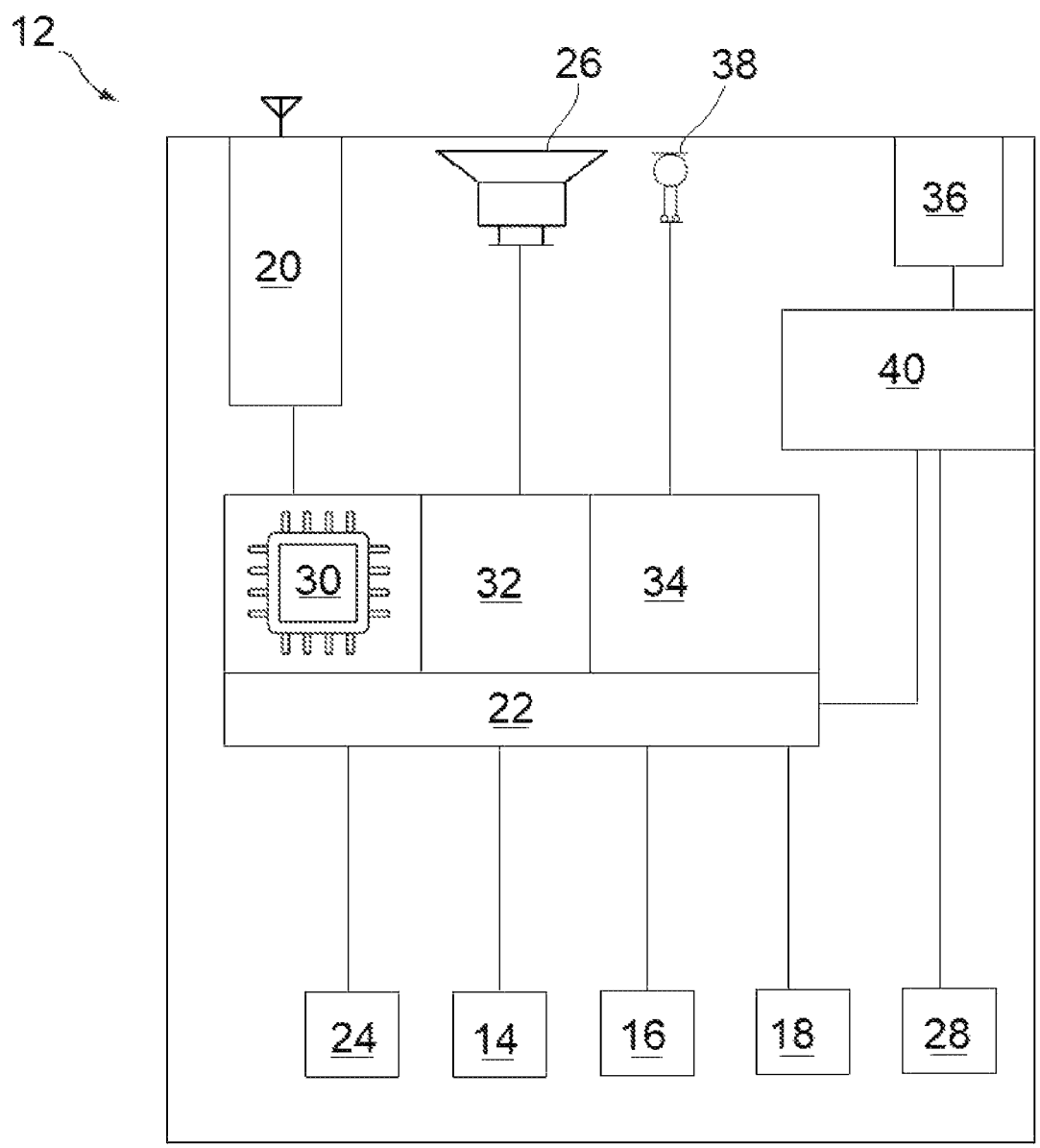
FIG. 3 is a schematic illustration of the child monitoring device.
Figure 4:
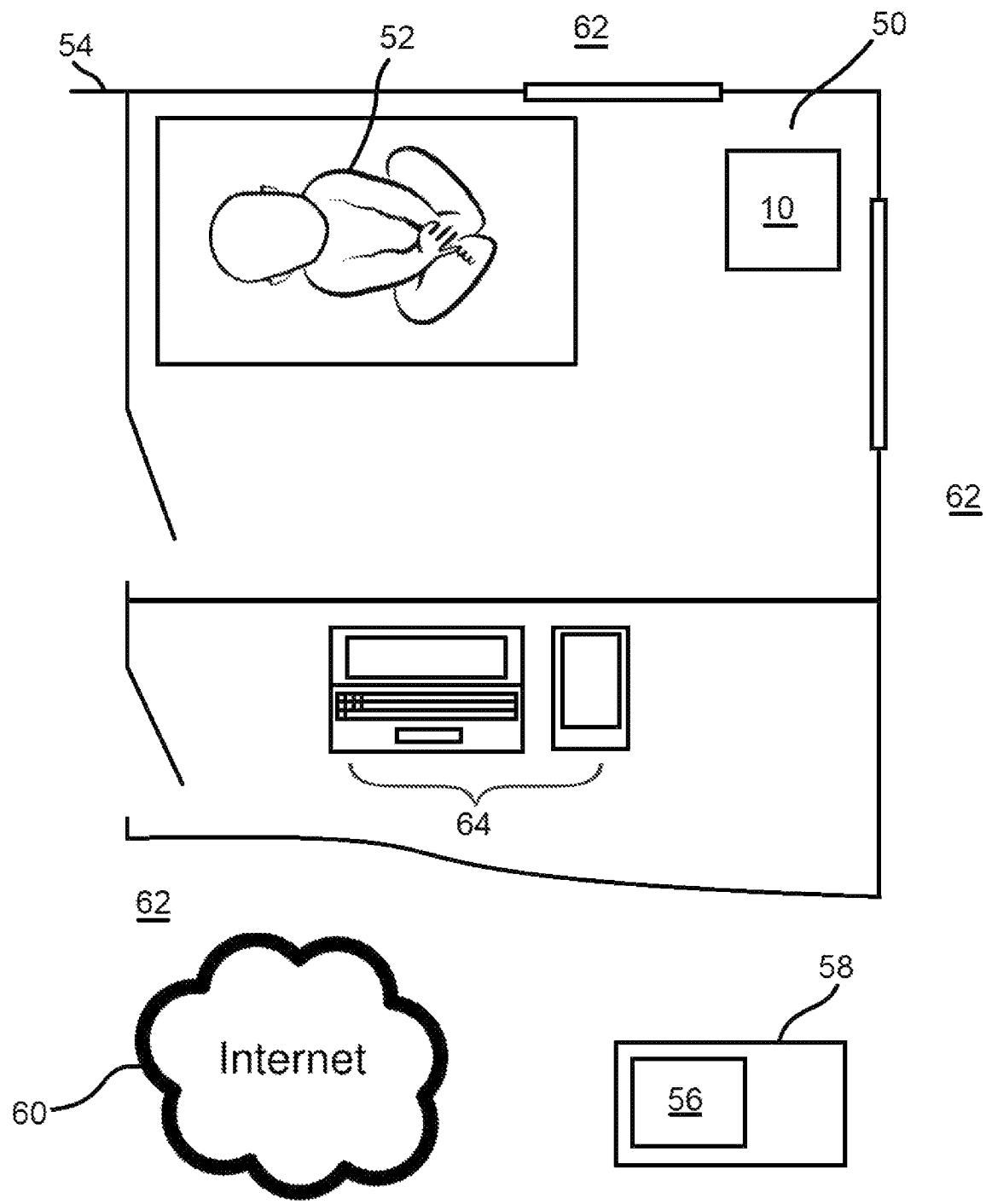
FIG. 4 is a schematic illustration of the child monitoring device in use.

Referring to FIGS. 3 and 4 a child monitoring device 12 that may be incorporated in a toy, such as the toy 10, may comprise at least one environmental sensor 14, 16, 18, a wireless communications unit 20 and a processing unit 22.

The at least one environmental sensor may include one or more air quality sensors 14, a temperature sensor 16 and a humidity sensor 18. There may be one or a plurality of air quality sensors 14, which may include a particulate sensor such as a PM2.5 particulate sensor, a carbon monoxide sensor, a carbon dioxide sensor and a volatile organic compound (VOC) sensor. The VOC sensor may be capable of detecting polluting gases such as ammonia, benzene vapours, ethanol, smoke, sulphides or other harmful gases.

The child monitoring device 12 may comprise an image capturing device 24. The image capturing device 24 may be a video camera or a stills camera with infrared night vision capability. The toy 10 may be positioned so that the image capturing device 24 can capture images of a child when asleep in its cot or bed.

The child monitoring device 12 may further comprise an audio output device 26. The audio output device 26 may comprise a built-in audio speaker. Alternatively, or additionally, the audio output device 26 may comprise an audio outlet, such as a jack plug socket, to which a remote audio speaker may be connected. The processing unit 22 may be configured to process audio signals downloaded via the wireless communications unit 20, including a codecs and amplification circuitry.

Figure 2:
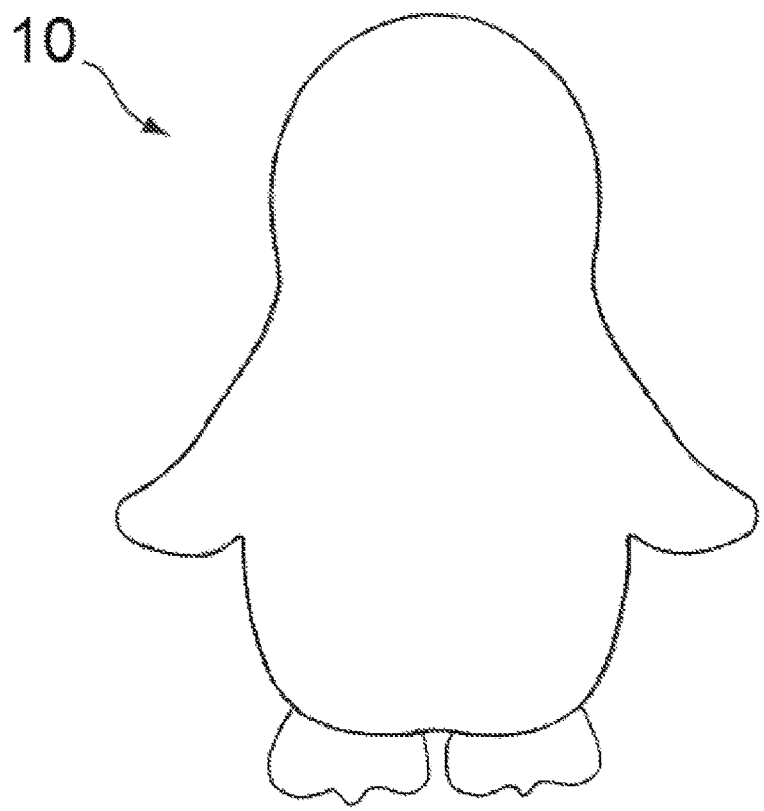
FIG. 2 is a view from the rear of the toy of FIG. 1.

The child monitoring device 12 may further comprise an air mover 28 configured to cause air movement around the at least one environmental sensor 14, 16, 18. In examples of the toy 10 in which an air mover 28 is provided, the body of the toy may be provided with a plurality of air intake apertures 30 (FIG. 2). The inner side of the body of the toy 10 may be provided with ribs, or other protuberances, configured to channel the air drawn through the intake apertures 30 by the air mover 28 towards the at least one environmental sensor 14, 16, 18. Although not shown in FIGS. 1 and 2, the body of the toy 10 may additionally comprise air outlet apertures or the like through which air drawn through the intake apertures 30 may escape the body of the toy.

The wireless communications unit 20 may comprise a transceiver configured to connect to the internet wirelessly using a WIFI protocol. The wireless communications unit 20 may also comprise a short-range communications transceiver able to communicate using a Bluetooth® protocol, or another suitable short-range communications protocol. The wireless communications unit 20 is connected with the processing unit 22 so as to be able to communicate incoming signals to the processing unit and transmit commands, data or requests from the processing unit 22 to a remote device, such as a cloud server or a mobile communications device. In this context, a mobile communications device may comprise a smartphone, tablet, laptop computer or the like.

The processing unit 22 may comprise one or more processors 30, permanent memory 32 and volatile memory 34. The processing unit 22 may also comprise suitable signal conditioning circuitry or the like to enable the processing unit to transmit and receive, as appropriate, signals to or from the various devices of the child monitoring device 12 to which it is connected. The permanent memory 32 is loaded with software or firmware to enable it to interact with the various devices of the child monitoring device 12 to which it is connected. The permanent memory 32 is also loaded with software, or an app, which when operated by the processing unit 22 enables the child monitoring device to perform child monitoring tasks.

The child monitoring device 12 may further comprise a nightlight 36, a microphone 38 and a power supply unit 40. The microphone 38 may be connected with the processing unit 22. The microphone 38 may be activated by the processing unit 30 according to stored settings or by a command signal received via the wireless communications unit 20. The processing unit 22 may be configured to monitor signals received from the microphone 38 and analyse the received signals to determine whether a child that is being monitored is in distress. If it is determined that the child is in distress, the processing unit 22 may cause the wireless communications unit 20 to transmit a message to one or more mobile communications devices to warn a parent, child minder or other suitable person that the child is in need of attention. Some or all of the messages transmitted by the wireless communications unit 20 may be transmitted directly to the receiving device or to a cloud service for onward transmission to the receiving device or receiving devices for which they are intended. Alternatively, or additionally, the messages may be transmitted to a cloud-based system for storage from where they can be accessed by persons having a suitable account.

Referring to FIG. 4, the toy 10 is shown located in an indoor space 50 to monitor a child 52. The indoor space 50 may be a bedroom or nursery that forms a part of a home 54. The home 54 may, without limitation, be a house, apartment or the like.

In use, the at least one environmental sensor 14, 16, 18 outputs signals representative of environmental conditions in the indoor space 50. The signals from the at least one environmental sensor 14, 16, 18 are received by the processing unit 22, which processes the signals to determine one or more indoor space air quality conditions. The processing unit 22 causes the wireless communications unit 20 to transmit a request to download data from an external database, which may be stored in a memory 56 of a cloud server 58. The wireless communications unit 20 communicates with the cloud server 58 over the internet 60 using a WIFI protocol and requests the download of data indicative of an outdoor air quality condition at the outdoor location 62 at which the indoor space is located. The indoor air quality condition may then be compared with the data representative of the outdoor air quality condition and a comparison may be made with data relating air quality to child development to determine whether the indoor air quality condition falls within predetermined limits. If the indoor air quality falls outside the acceptable predetermined limits, the processing unit 22 may cause the wireless communications unit 20 to transmit a message or messages containing information relating to the disparity, including messages indicating adjustments or actions to be taken that may bring the indoor air quality condition within the predetermined limits, or at least make it tend towards that position. Some or all of the messages transmitted by the wireless communications unit 20 may be transmitted directly to the receiving device or to a cloud service for onward transmission to the receiving device or receiving devices for which they are intended. Alternatively, or additionally, the messages may be transmitted to a cloud-based system for storage from where they can be accessed by persons having a suitable account.

The processing unit 22 may also be configured so that it can receive and process data relating to a child that is to be monitored that is input via the wireless communications unit

20. The data may be input by a parent using a mobile communications device 64, such as a laptop computer, smartphone or tablet. The input data may comprise at least one of:
  i) height;
  ii) weight;
  iii) a health event;
  iv) vocal expressions of the child; and
  v) own movements of the child.

In some examples, data input may be automatic or semi-automatic. For example, data relating to weight entry may be by wireless transmission from scales equipped to wirelessly transmit weight data using, for example, a WIFI protocol. In some examples, vocal expressions of the child may additionally, or alternatively, be automatically recorded. The processing unit 22 may be configured to make recordings during periods in which the child is expected to sleep and analyse the results to determine sleep behaviour of the child, such as how many times it wakes. Thus, for example, a parent may input commands via the mobile communications device 64 to cause the microphone 38 to become active during a predetermined period.

The input data relating to the child may be stored locally in the permanent memory 32 of the processing unit 22 or transmitted to a cloud storage server 58 and stored in a database linked to an account specific to the child 52. The processing unit 22 is configured to cause the wireless communications unit 20 to send messages to the cloud storage server 58 requesting generalised child development data held in a specialised database stored on the server. The processing unit 22 may process the input data relating to the child and compare it with the generalised child development data received from the cloud storage server 58 and determine whether the child's development falls within normal, or acceptable, limits. The processing unit 22 may then cause the wireless communications unit 20 to transmit one or more messages containing the results of the comparison. Additionally, or alternatively, the processing unit 22 may cause the wireless communications module 20 to transmit one or more messages indicating measures that may be taken to improve the child's development. Some or all of the messages transmitted by the wireless communications unit 20 may be transmitted directly to the receiving device or to a cloud service for onward transmission to the receiving device or receiving devices for which they are intended. Alternatively, or additionally, the messages may be transmitted to a cloud-based system for storage from where they can be accessed by persons having a suitable account.

The processing unit 22 may be configured to cause the image capturing device 24 to operate to capture images of the child 52. The processing unit 22 may be configured to analyse the images captured by the image capturing devices 24 to determine sleep patterns of the child 52. The processing unit 22 may be configured to compare the determined sleep patterns against generalised, or normal, sleep pattern data contained in a database and determine whether the determined sleep patterns are within predetermined limits. To enable this comparison to be made, the processing unit 22 may be configured to cause the wireless communications unit 20 to request the download of normalised sleep data from an external database stored in the cloud based server 58. If the comparison of the determined sleep patterns and normalised sleep data indicates that the child 52 has sleep patterns outside of normal, or acceptable, predetermined limits, the processing unit 22 may cause the wireless communication unit 20 to transmit messages containing information about the child's sleep patterns, which may include suggestions for improving the child's sleep patterns. Some or all of the messages transmitted by the wireless communications unit 20 may be transmitted directly to the receiving device or to a cloud service for onward transmission to the receiving device or receiving devices for which they are intended. Alternatively, or additionally, the messages may be transmitted to a cloud-based system for storage from where they can be accessed by persons having a suitable account.

The processing unit 22 may be configured to cause the wireless communications unit 20 to stream audio content that is output via the audio output device 26. The audio content may comprise music, stories or messages recorded by the child's parents. Additionally, or alternatively, the audio output may comprise one or more of recorded heartbeats, for example, the mother's heartbeat, sounds to promote relaxation and sounds to promote cognitive development. Sounds to promote cognitive development may include sounds may include own age appropriate auditory enrichment curriculum designed to encourage early learning for children aged 0 to 3 years, such as the auditory enrichment curriculum marketed by The BabyPlus Company LLC under the registered trade marks NurseryNotes and ToddlerTunes.

The processing unit 22 may be configured to operate AI functionality. Thus, the software, or an app, loaded into the permanent memory 32 of the processing unit 22 may include a known algorithm that analyses at least one of the data acquired from the sensors, the input data relating to the child and the data received from external databases and based on logical results, verify whether the data is consistent with normal expectations so that erroneous data may be identified. If the data verification indicates that the data is acceptable, the analysis of the data may then determine whether the indoor air quality condition or child development conditions that are indicated are acceptable or there are problems to be addressed and what factors could influence the problems.

The child monitoring device together with the software, or app, may be configured to interact with Eco systems like Amazon Alexa, Google Assistant or Apple Siri.

In some examples, the wireless communications module may be operated in notification module. In this mode, the wireless communications module will only switch on when a data processing process is to be initiated or information needs to be transmitted to external devices. Otherwise, the wireless communications module is kept off, so that no radiation is emitted.

In some examples, the processing unit 22 may be configured to cause the image capturing device 24 to function in monitoring mode in which the image capturing device operates continuously over a predetermined period.

In the illustrated examples, the child monitoring device is described as being incorporated in a toy. It is to be understood that this is not essential. For example, the child monitoring device may be incorporated in other products such as an audio player or a night light. In other examples, the child monitoring device may be a dedicated standalone device.

In the illustrated examples, the child monitoring device is provided with a wireless communications unit to enable communication with external devices such as a mobile communications device of a parent or other child carer and a cloud-based server. In other examples, the child monitoring device may be provided with a card, or other suitable circuitry, to allow connection to the internet via a wired connection.

In the illustrated examples, the data analysis is performed by the processing unit. In some examples, the processing unit may be configured to upload data to the cloud-based server 58 so that the data analysis can be carried out on the server.

The child monitoring device and cloud-based server, or other cloud-based system, may form a child monitoring system. The cloud-based server may store, or access, specialised databases from which data may be downloaded by the child monitoring device. The specialised databases may include one or more air quality databases, one or more pediatrics databases and databases incorporating statistical child development data.

The invention claimed is:

1. A child monitoring device comprising:
   at least one environmental sensor to output signals representative of an environmental condition in an indoor space in which the child monitoring device is located;
   a wireless communications unit; and
   a processing unit,
   wherein said processing unit is configured to:
      receive said signals from said at least one environmental sensor and process said signals to determine an indoor space air quality condition,
      cause said wireless communications unit to wirelessly communicate with an external database to receive data indicative of an outdoor air quality condition at a location at which said indoor space is located and data correlating air quality to child development,
      process said indoor air quality condition, outdoor air quality condition and data relating air quality of child development to determine whether said indoor air quality condition is within predetermined limits, and
      if said indoor air quality is not within said predetermined limits cause said wireless communications unit to output messages indicating adjustments to cause a change in said indoor space air quality condition to provide an indoor space air quality condition that is within said predetermined limits.

2. A child monitoring device as claimed in claim 1, further comprising an air mover configured to cause air movement around said at least one sensor.

3. A child monitoring device as claimed in claim 1, wherein said at least one environmental sensor comprises at least one of:
   i) an air quality sensor;
   ii) a temperature sensor; and
   iii) a humidity sensor.

4. A child monitoring device as claimed in claim 3, wherein said air quality sensor comprises:
   i) a particulate matter sensor;
   ii) a carbon monoxide sensor;
   iii) a carbon dioxide sensor; or
   iv) a volatile organic compounds sensor.

5. A child monitoring device as claimed in claim 1, further comprising an image capturing device to capture images of said child and said processing unit is configured to analyze said images to determine sleep patterns of said child.

6. A child monitoring device as claimed in claim 5, wherein said processing unit is configured to compare said determined sleep patterns against sleep pattern data contained in a database and determine whether said determined sleep patterns are within predetermined limits.

7. A child monitoring device as claimed in claim 1, further comprising an audio output device, wherein said processing unit is configured to cause said audio output device to output audio comprising at least one of:
   i) music;
   ii) stories;
   iii) audio messages from a parent;
   iv) sounds to promote relaxation;
   v) recorded heartbeats; and
   vi) sounds to promote child cognitive development.

8. A child monitoring device as claimed in claim 7, wherein said processing unit is configured to cause said wireless communications unit to download said output audio from an external source.

9. A child monitoring device as claimed in claim 1, wherein said processing unit is configured to run an AI process to verify at least one of said indoor space air quality condition and said outdoor quality condition prior to determining whether said indoor air quality condition is within said predetermined limits.

10. A child monitoring device as claimed in claim 1, wherein said at least one environmental sensor, said wireless communications unit and said a processing unit are housed in a child's toy.

* * * * *